(12) United States Patent
Hossainy

(10) Patent No.: US 7,232,490 B1
(45) Date of Patent: Jun. 19, 2007

(54) APPARATUS AND METHOD FOR COATING STENTS

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 125 days.

(21) Appl. No.: 10/099,101

(22) Filed: Mar. 15, 2002

(51) Int. Cl.
*B05B 13/04* (2006.01)

(52) U.S. Cl. .......................................... 118/320; 118/64

(58) Field of Classification Search ................. 118/64, 118/65, 600, 302, 300, 500, 319, 324, 320, 118/322, 52, 66, 69, 62, 63, 56; 239/4, 102.2, 239/102.1; 427/2.24, 228, 2.25, 2.28; 623/1.46–1.48, 623/1.11; 606/192, 198, 194, 108; 269/47, 269/48, 43–45, 37
See application file for complete search history.

(56) References Cited

U.S. PATENT DOCUMENTS 3,067,948 A * 12/1962 Lang et al.
3,645,447 A * 2/1972 Cowan ........................ 239/692
4,733,665 A    3/1988 Palmaz ....................... 128/343
4,776,990 A * 10/1988 Verity
4,800,882 A    1/1989 Gianturco .................... 128/343
4,802,627 A *  2/1989 Moy et al. ................... 239/112
4,886,062 A   12/1989 Wiktor ........................ 128/343
5,437,726 A *  8/1995 Proto et al.
5,514,214 A *  5/1996 Joel et al.
6,056,993 A *  5/2000 Leidner et al. ............. 427/2.25
6,167,318 A * 12/2000 Kizer et al.
6,527,863 B1 *  3/2003 Pacetti et al. ............... 118/500
6,562,136 B1 *  5/2003 Chappa et al. .............. 118/500
6,682,771 B2 *  1/2004 Zhong et al. ............... 427/2.24
6,743,462 B1 *  6/2004 Pacetti ....................... 427/2.24

* cited by examiner

*Primary Examiner*—Brenda A. Lamb
(74) *Attorney, Agent, or Firm*—Squire, Sanders & Dempsey L.L.P.

(57) ABSTRACT

An apparatus for coating stents and a method of using the same is provided.

11 Claims, 3 Drawing Sheets

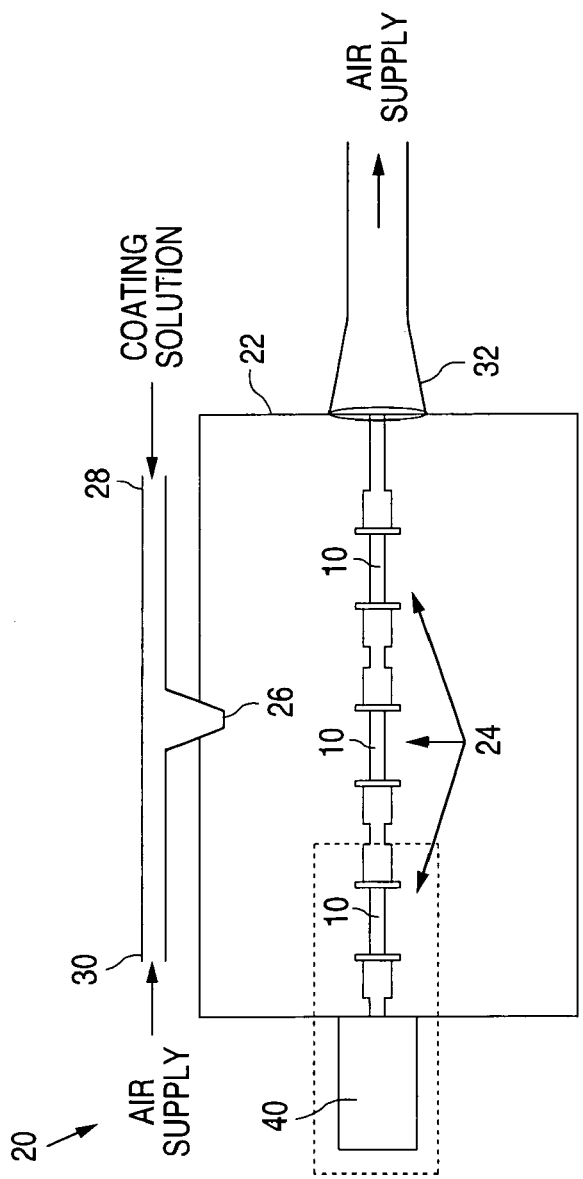
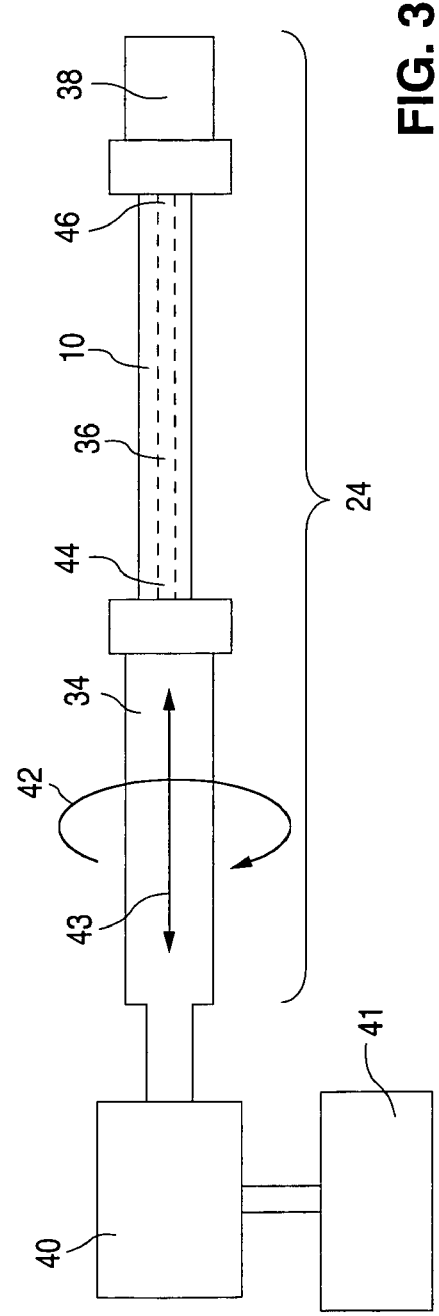

APPARATUS AND METHOD FOR COATING STENTS

TECHNICAL FIELD

This invention relates to stent coating systems and methods of coating stents.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

During the coating process, the therapeutic substance may be exposed to light, thereby damaging the therapeutic substance should the substance be photosensitive. Accordingly, a new apparatus and method for coating stents is needed for protection of the therapeutic substance. Additionally, it is also desirable that the apparatus be able to coat a large number of stents at one time, thereby increasing the manufacturing time of drug-eluting stents.

SUMMARY

A stent coating apparatus is provided including a chamber for housing a stent. The chamber is configured to prevent or significantly inhibit the exposure of the stent to light, for example ultraviolet, visible, or infrared light. The apparatus can include a nozzle for spraying a coating composition onto the stent. The coating composition can include a polymer dissolved in a solvent and optionally a therapeutic substance added thereto. The nozzle can generate atomized particles having an average size from about 20 to 30 µm. In one embodiment, a convection oven can be coupled to the nozzle for supplying warm air to the coating composition or the stent.

In accordance with another embodiment of the invention, a large-scale coating apparatus is provided having a coating chamber for housing a plurality of mandrel fixtures for holding stents. The mandrel fixtures can be positioned either in series or in a parallel configuration or a combination of both. A motor can be coupled to the mandrel fixtures for rotating the stents during the coating procedure. A nozzle penetrating into the chamber can spray a coating composition on the stents. The chamber can also include a blower for applying warm or cold gas, such as air, to the composition or the stents.

A method for coating stents is also provided including mounting a plurality of stents onto mandrel fixtures within a chamber of a coating apparatus and forming a coating on the stents. In one embodiment, the chamber does not allow the stents from being exposed to light, such as ultraviolet, visible or infrared light. Forming the coating can be performed by spraying a coating composition from a nozzle onto the stents. A warm gas, such as air, can be applied to the composition during the application of the composition from the nozzle. Additionally, a warm gas can be applied to the stents subsequent to the application of the composition.

BRIEF DESCRIPTION OF THE DRAWINGS

FIG. 2 illustrates a coating apparatus according to an embodiment of the invention;

FIG. 3 illustrates one embodiment of a stent mandrel fixture of the apparatus of FIG. 2.

DETAILED DESCRIPTION

Figure 1:
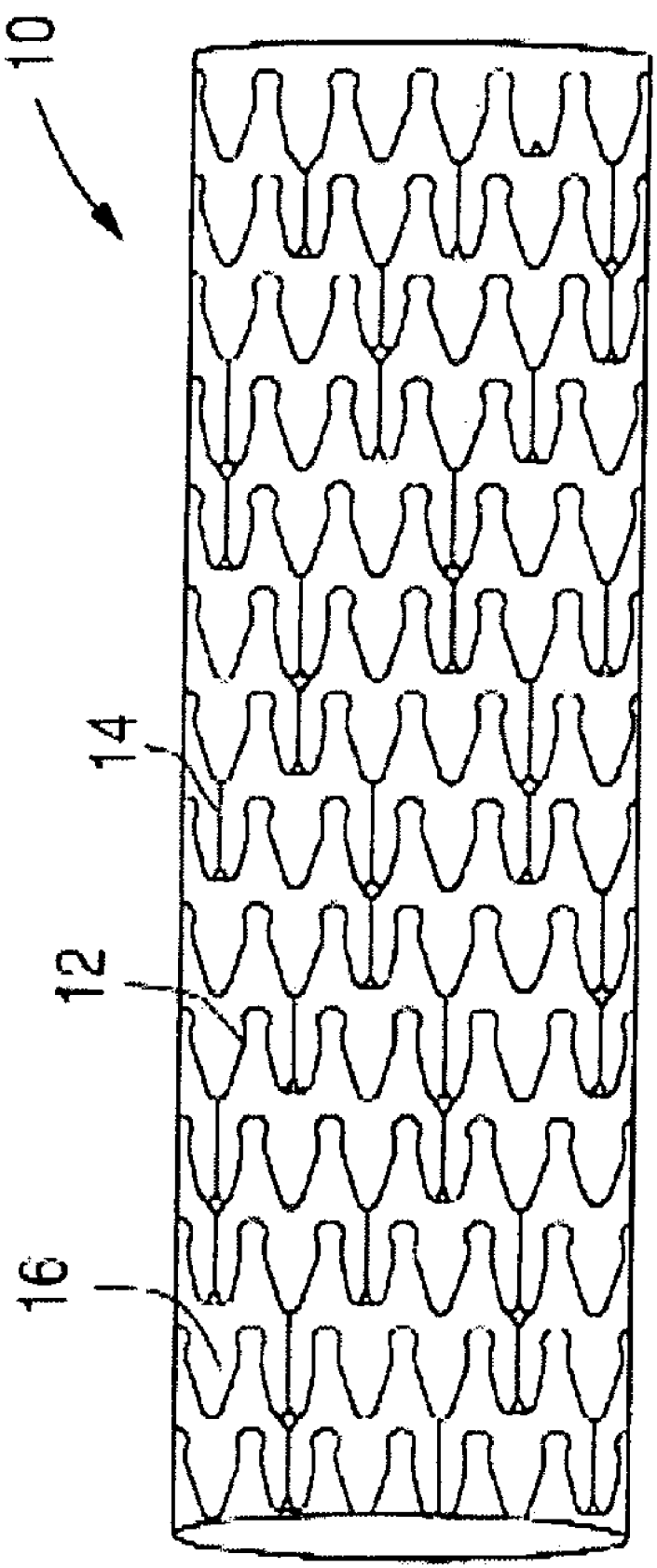
FIG. 1 illustrates a conventional stent.
Figure 4:
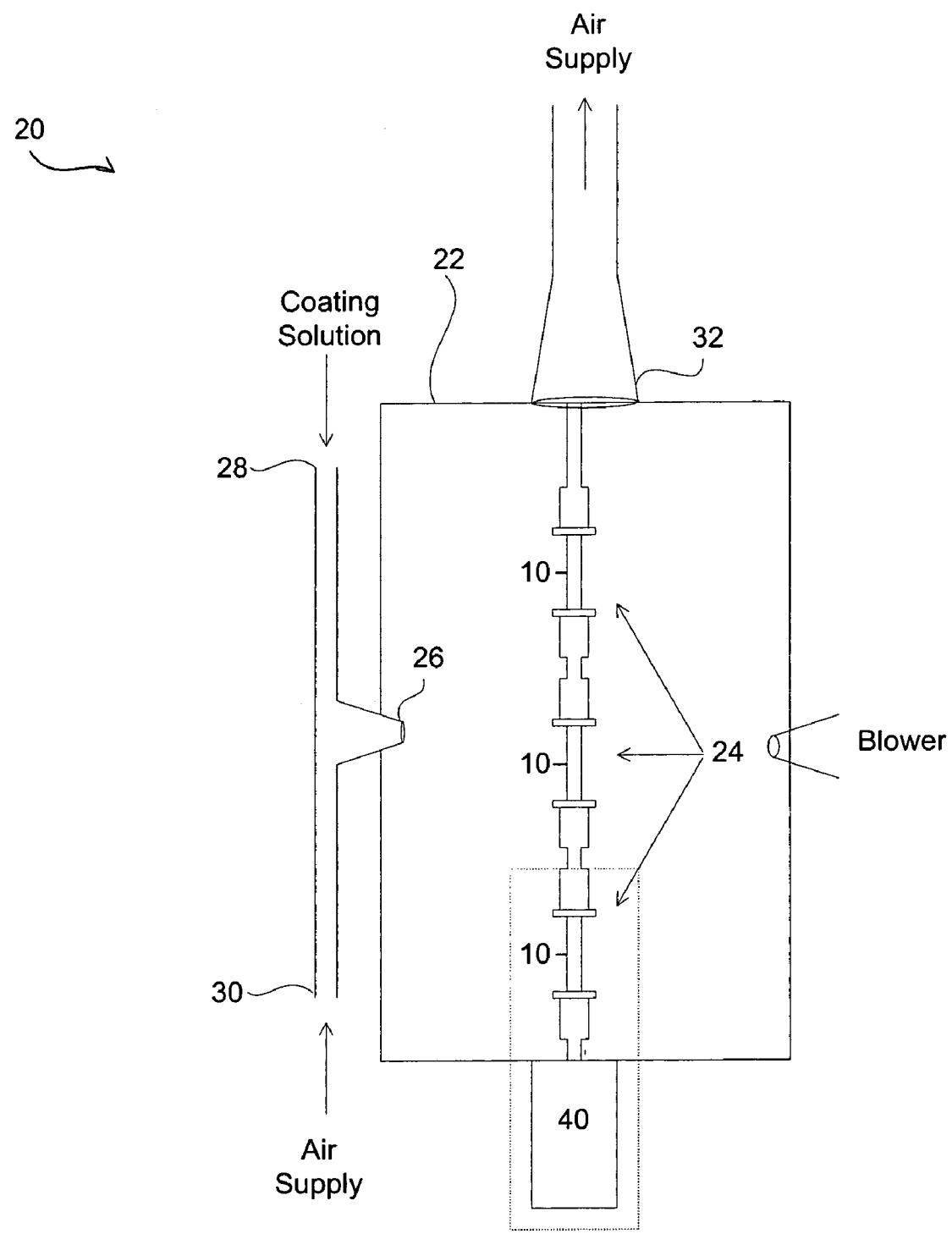
FIG. 4 illustrates a coating apparatus according to another embodiment of the invention.

FIG. 2 illustrates a stent coating apparatus 20 according to an embodiment of the invention. Apparatus 20 comprises a coating chamber 22 that can be impervious to light. Impervious to light is defined as significantly inhibiting or completely preventing light having any harmful frequency and wavelength from penetrating into chamber 22. More particularly, in one embodiment, ultraviolet, visible, and/or infrared light should be inhibited or prevented from penetrating into chamber 22. Apparatus 20 includes a plurality of stent mandrel fixtures 24 for holding and rotating stents 10 during application of the coating composition, as will be described in further detail in conjunction with FIG. 3. While the embodiment of FIG. 2 shows three fixtures 24 positioned in series, any number of fixtures 24 can be used. Additionally, fixtures 24 can be positioned in a parallel configuration with respect to one another. Fixtures 24 may be positioned either in the horizontal or vertical plane within apparatus 20.

Apparatus 20 additionally includes a spray nozzle assembly 26 penetrating inside chamber 22. Nozzle assembly 26 can be in fluid communication with one or multiple coating composition sources via an inlet 28. Multiple composition sources allow a variety of coating compositions to be applied to stents 10, for example in a time delay or time synchronized fashion. Nozzle assembly 26 can also be coupled to a convection oven or a blower (not shown) via an inlet 30 for application of warm (e.g., above room temperature) or cold (e.g., below room temperature) gas, such as air, to the composition and/or stents 10. In one embodiment, nozzle assembly 26 is capable of generating atomized particles of about 20–30 µm in size. The particle size should not be too small because it may lead to drying rather than to spray coating. Due to Joule-Thompson expansion at nozzle assembly's 26 outlet, the coating composition may cool, leading to precipitation of the polymer. Accordingly, when applying coating compositions that precipitate out, warm air from the convection oven via inlet 30 may be used during the coating application to heat the composition to prevent precipitation.

In an embodiment of the invention, after a coating process has been completed, warm air from the convection oven may be passed over stents 10 to dry the coating. The convection air can then exit chamber 22 via an outlet 32.

FIG. 3 illustrates fixture 24 in accordance with an embodiment of the invention. Fixture 24 for supporting stent 10 is illustrated to include a support member 34, a mandrel 36, and a lock member 38. Support member 34 can connect to a motor 40 so as to provide rotational motion about the longitudinal axis of stent 10, as depicted by arrow 42, during the coating process. Another motor 41 can also be provided for moving support member 34 in a linear direction 43.

Support member 34 can also include a bore (not shown) for receiving a first end 44 of mandrel 36. First end 44 of mandrel 36 can be threaded to screw into the bore or, alternatively, can be retained within the bore by a friction fit. The bore should be deep enough so as to allow mandrel 36 to securely mate with support member 34. The depth of the bore can also be over-extended so as to allow a significant length of mandrel 36 to penetrate or screw into the bore. This would allow the length of mandrel 36 to be adjusted to accommodate stents of various sizes.

The outer diameter of mandrel 36 can be smaller than the inner diameter of stent 10 so as to prevent the outer surface of mandrel 36 from making contact with the inner surface of stent 10. A sufficient clearance between the outer surface of mandrel 36 and the inner surface of stent 10 should be provided to prevent mandrel 36 from obstructing the pattern of the stent body during the coating process. By way of example, the outer diameter of mandrel 36 can be from about 0.010 inches (0.254 mm) to about 0.017 inches (0.432 mm) when stent 10 has an inner diameter of between about 0.025 inches (0.635 mm) and about 0.035 inches (0.889 mm).

A second end 46 of mandrel 36 can be permanently affixed to lock member 38 if first end 44 is disengagable from support member 34. Alternatively, in accordance with another embodiment, mandrel 36 can have a threaded second end 46 for screwing into a bore (not shown) of lock member 38. This bore can be of any suitable depth that would allow lock member 38 to be incrementally moved closer to support member 34. Fixture 24 allows stents 10 of any length to be securely pinched between support and lock members 34 and 38. In accordance with yet another embodiment, a non-threaded second end 46 and bore combination can be employed such that second end 46 can be press-fitted or friction-fitted within the bore to prevent movement of stent 10 on stent mandrel fixture 24.

The coating composition can include a solvent, a polymer dissolved in the solvent and optionally a wetting fluid added thereto. The composition can also include therapeutic substances or active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and combinations thereof.

A wetting fluid can be used to enhance the wetting of the composition or to increase the capillary permeation of the composition. Capillary permeation is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. Representative examples of wetting fluid include tetrahydrofuran (THF), dimethylformamide (DMF), 1-butanol, and n-butyl acetate.

The active agent could be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Exposure of the active ingredient to the composition should not adversely alter the active ingredient's composition or characteristic. Accordingly, the particular active ingredient is selected for compatibility with the solvent or blended polymer-solvent.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent coating apparatus, comprising:
    a coating chamber housing a first stent support and a second stent support for supporting stents, the first and second stent supports positioned with respect to one another in an adjacent serial configuration such that one end of the first stent support extends from an end of the adjacent second stent support;
    a motor coupled to the first stent support such that the rotation of the first stent support can allow for rotation of the second stent support; and
    a spray nozzle for spraying a coating composition onto the stents.

2. The apparatus of claim 1, wherein the coating chamber does not allow ultraviolet, visible or infrared light from penetrating into the chamber.

3. The apparatus of claim 1, wherein the coating chamber additionally comprises a blower for applying warm or cold gas to the stents.

4. The apparatus of claim 1, wherein the stents are positioned vertically in the coating chamber.

5. The apparatus of claim 1, wherein the stents are positioned horizontally in the coating chamber.

6. The apparatus of claim 1, additionally including a second motor communicatively coupled to the stent supports for moving the stents linearly passed the spray nozzle.

7. The apparatus of claim 1, wherein the applicator spray nozzle is capable of being in communication with multiple coating composition sources.

8. The apparatus of claim 1, additionally including means for circulating a gas or air within the chamber.

9. The apparatus of claim 1, additionally including a blower to blow a gas onto the stents.

10. The apparatus of claim 1, wherein the chamber can operate as a convection oven.

11. The apparatus of claim 1, wherein the spray nozzle is capable of being in communication with multiple coating composition sources for applying different coating compositions to the stents in a time delay or time synchronized fashion.

* * * * *